United States Patent [19]

Hilleman et al.

[11] 4,022,206
[45] May 10, 1977

[54] VACCINE DELIVERY SYSTEM

[75] Inventors: Maurice R. Hilleman, Lafayette Hill; William J. McAleer, Ambler, both of Pa.

[73] Assignee: Merck & Co., Inc., Rahway, N.J.

[22] Filed: Aug. 1, 1975

[21] Appl. No.: 600,983

[52] U.S. Cl. .............................. 128/216; 128/272; 206/365; 229/3.5 MF
[51] Int. Cl.² ........................................ A61M 5/00
[58] Field of Search .......... 128/216, 215, 217, 218, 128/272, 214, 221, DIG. 24; 206/364–370, 438–441; 229/3.5 MF

[56]  References Cited
UNITED STATES PATENTS

| 2,726,656 | 12/1955 | Lockhart | 128/216 |
|---|---|---|---|
| 2,895,475 | 7/1959 | Cole | 128/272 |
| 3,158,283 | 11/1964 | Rinfret et al. | 128/272 X |
| 3,286,832 | 11/1966 | Pilger | 206/365 |
| 3,325,059 | 6/1967 | Hein | 128/272 X |
| 3,337,041 | 8/1967 | Damaskus | 128/272 |
| 3,472,369 | 10/1969 | Schuster | 206/438 X |

*Primary Examiner*—John D. Yasko
*Attorney, Agent, or Firm*—Donald J. Perrella; J. Jerome Behan

[57] ABSTRACT

Vaccine delivery system having a lyophilized vaccine in human dosage concentration loaded into presterilized single dosage syringe having a squeezable body portion and a separate package containing enough water for injection to reconstitute the single dose of lyophilized vaccine.

12 Claims, 9 Drawing Figures

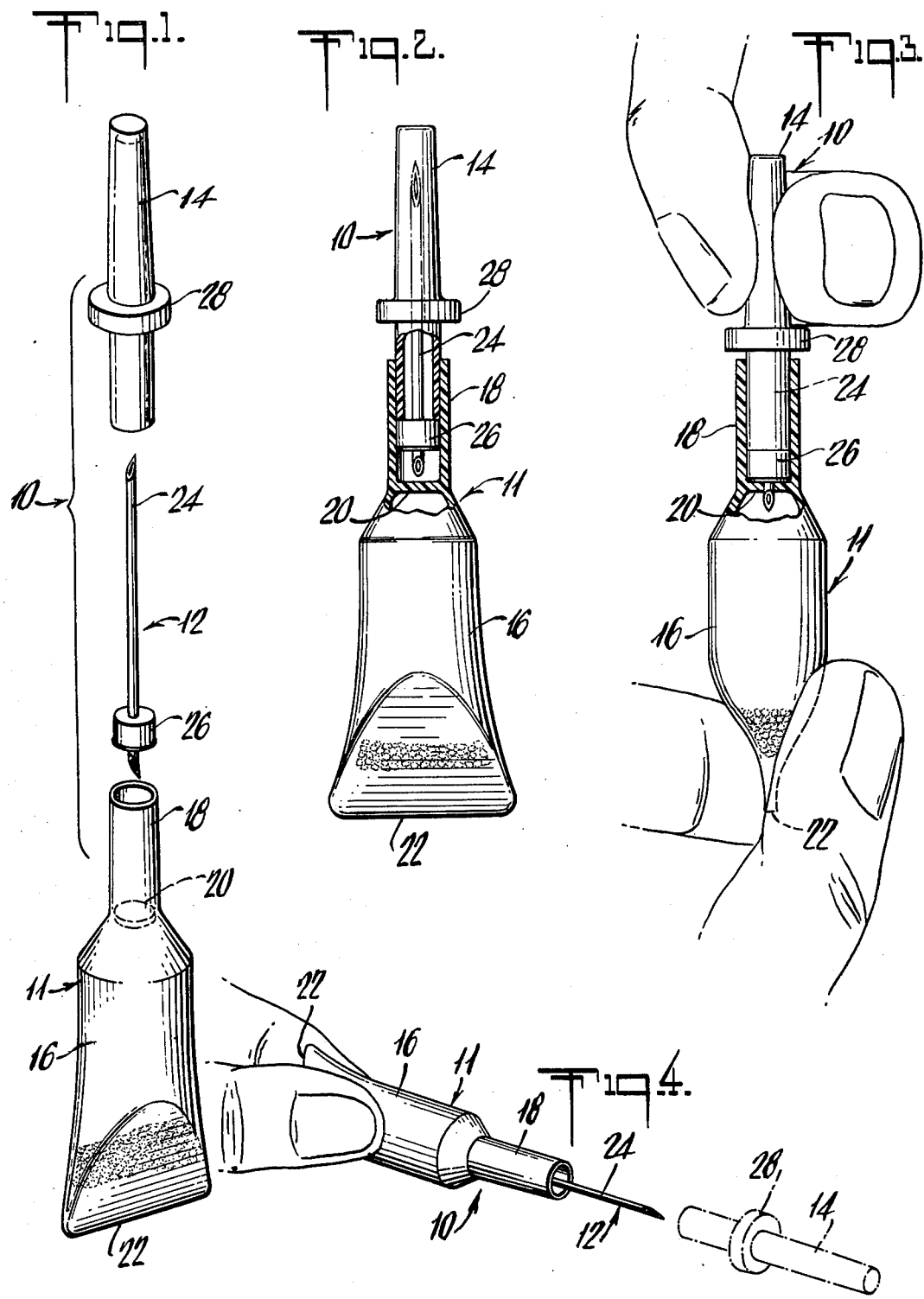

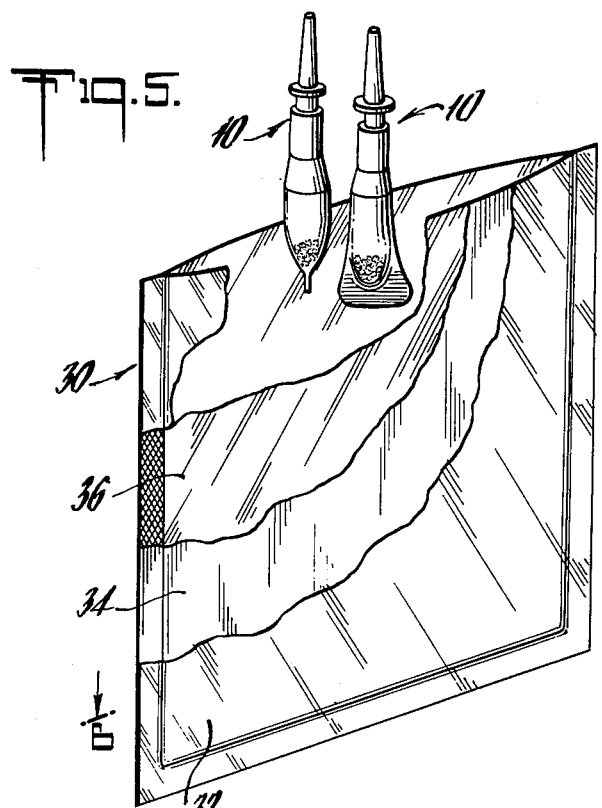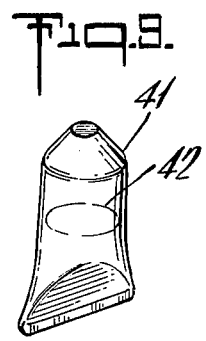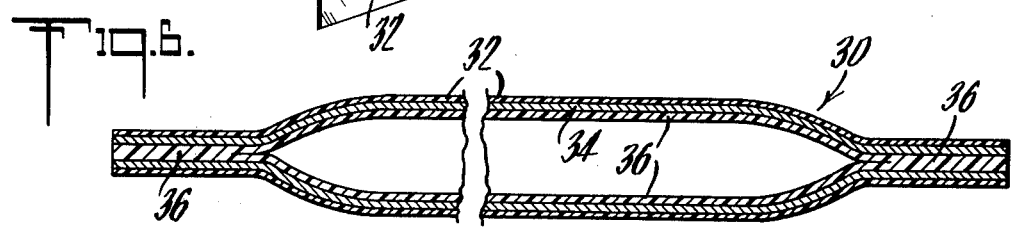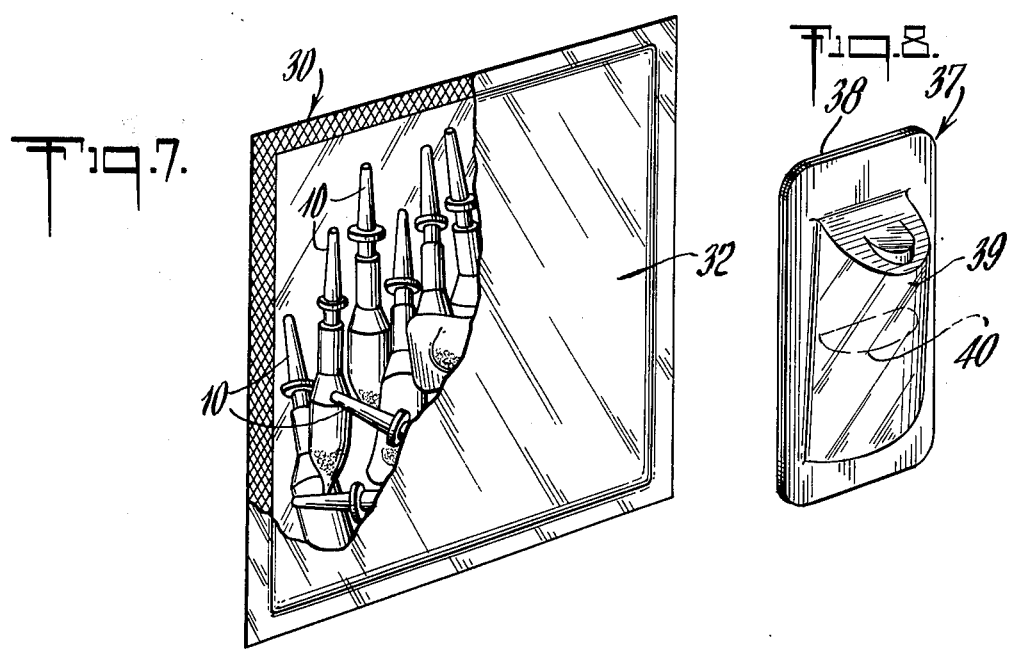

VACCINE DELIVERY SYSTEM

BACKGROUND OF THE INVENTION

1. Field of the Invention

This invention relates to the delivery of vaccines and more particularly it concerns novel methods and apparatus for packaging and dispensing vaccines of the type which are administered by injection through a needle.

2. Description of the Prior Art

In general, vaccines, after being harvested from a culture tank, are clarified, diluted, subdivided into vials or ampules and then lyophilized. When lyophilized the vaccine may be kept for extended periods of time at a temperature not above about 8° C, typically from about −20° C. to about 8° C, with losses substantially below those encountered in aqueous vaccines. A long unmet need has been the providing of a low cost single dose delivery system for a lyophilized vaccine.

OBJECTS OF THE INVENTION

It is an object of the present invention to provide an improved delivery system for a lyophilized vaccine. Another object is to provide a simple, uncomplicated and inexpensive single dose delivery system for a llyophilized vaccine. These and other objects of the present invention will be apparent from the following description.

SUMMARY OF THE INVENTION

According to the present invention, there is provided a novel single dosage vaccine delivery system including a hypodermic syringe which comprises a container portion, a needle portion and a dust guard for the needle portion. The container portion is made of a plastic material which is flexible and resilient at room temperature. The container portion is filled with a single dose of lyophilized vaccine suitable for human administration.

According to a further aspect of the invention, there is provided a novel package arrangement wherein a plurality of vaccine containing syringes, as above described, are maintained together in a gas, moisture and light impervious bag or pouch (such as a metal foil bag) which protects the vaccine in the syringes from the deteriorating effects of light, moisture and carbon dioxide gas.

According to a still further aspect of the invention, there is provided a novel method of preparing vaccine for storage, delivery and administration. This method involves filling sterilized syringes with an aqueous vaccine diluted to human dosage concentration, freezing the aqueous vaccine in the unsealed syringe, lyophilizing the frozen aqueous vaccine, and sealing the syringe under anhydrous conditions, and then sealing a plurality of the syringes inside a gas, moisture and light impervious bag or pouch. Preferably, a dessicant is present. The bag or pouch (such as a metal foil bag) is then subjected to a low temperature.

BRIEF DESCRIPTION OF THE DRAWINGS

Several embodiments of the invention have been chosen for purposes of illustration and description, and are shown in the accompanying drawings, forming a part of the specification, wherein:

FIG. 1 is an exploded perspective view of a syringe portion of a vaccine delivery system according to the present invention;

FIG. 2 is a front elevational view, partially cut away, of the syringe of FIG. 1 in assembled condition;

FIG. 3 is a side elevational view of the syringe of FIG. 2 during a readying operation;

FIG. 4 is an exploded perspective view showing the syringe of FIG. 3 in condition for an injection operation;

FIG. 5 is a perspective view, partially cut away, showing a container for holding syringes according to the present invention;

FIG. 6 is an enlarged sectional view taken along line 6—6 of FIG. 5;

FIG. 7 is a front elevational view, partially cut away, showing a syringe and container assembly according to the present invention; and FIGS. 8 and 9 are a perspective view of differing containers for water for injection.

DETAILED DESCRIPTION OF THE PREFERRED EMBODIMENTS

FIGS. 1–4 show a syringe 10, which is generally similar to those shown and described in U.S. Pat. Nos. 1,687,502, 2,642,064 and 2,693,183.

As can be seen in FIG. 1, the syringe 10 comprises a container portion 11, a needle portion 12 and a dust guard 14. The container portion 11 is made of a soft plastic material which is resiliently flexible at room temperature. This material must be capable of remaining stable at low temperatures, i.e., not above about 8° C., typically from about −20° C to about 8° C, and most typically from about 5° C. to about −5° C or below, and of recovering its resilient flexibility when returned to room temperature. Also, the material of the container portion 10 should be permeable to a gas sterilizing atmosphere such as ethylene oxide. Low density polyethylene has been found to be quite suitable for this purpose, although other plastics are equally useful.

The container portion 11 has a generally tabular main body region 16 which tapers inwardly at its upper end to a hollow cylindrical neck 18. A diaphragm 20 extends across the lower end of the neck 18 to close off the main body region 16. The lower end of the main body region is flattened and heat sealed closed as indicated at 22.

The needle portion of the syringe is conventional and consists of a hollow sharp needle for injection. The dust guard protects the needle portion of the syringe and helps to insure sterility. It may be made out of any type of the more rigid plastics such as polyethylene, polypropylene, polyesters or the like. The needle portion 12 comprises a hollow elongated needle 24 which extends through, and is press fitted in, a metal collar 26. The needle 24 is cut on a bias at both ends to form penetrating points; in the one case, for injection into a patient, and in the other case, for piercing the diaphragm 20. The collar 26 is dimensioned to fit snugly but slideably in the cylindrical neck 18 as illustrated in FIG. 2.

The dust guard 14 is molded of a plastic material, such as polyethylene, nylon or polypropylene, which may be somewhat harder than the material of the container portion 10. The dust guard 14 is also of generally tubular configuration and is closed at its upper end and open at its lower end. A flange 28 is formed about the mid-portion of the dust guard. The region below the flange 28 as shown in FIG. 2, also fits snugly but slideably inside the neck 18 of the container portion 10. As can be seen, the dust guard 14 is of sufficient length to accommodate the needle 24 when the lower end of the dust guard presses against the collar 26. It will also be noted that the flange 28 is at a greater distance above the upper end of the neck 18 than the distance between the lower end of the needle 24 and the diaphragm 20.

The syringe assembly as shown in FIG. 2, maintains a lyophilized vaccine sealed in the main body region 16 of the container portion 10. To ready the syringe for an injection, the dust guard 14 is pushed down into the neck 18 to force the collar 26 and needle 24 downwardly until the lower end of the needle pierces the diaphragm 20 and opens into the main body region 16. The dust guard 14 is then removed, as shown in FIG. 4, and the needle inserted into a container of water for injection and a quantity of the water sufficient to reconstitute the lyophilized vaccine is drawn into the syringe. The syringe is then ready for the administration of a dose of vaccine. The vaccine is administered by injecting the outer end of the needle 24 into a patient and then squeezing the main body region 16 to force the vaccine out through the needle.

In the present invention, the syringe is prepared for reception of vaccine by assembling the needle portion 12 and dust guard 14 to the container portion 10. At this time, however, the lower end of the container portion is open. The syringe is then sterilized by exposing it to an atmosphere of ethylene oxide at 50 percent relative humidy at a temperature of about 135° F. and at a pressure of between 8-10 psig, for a period of about 56 hours. The ethylene oxide gas permeates the polyethylene material of the syringe and the polypropylene material of the syringe and the polyproplyene material of the dust guard 14 so that the entire syringe becomes sterilized without fear of contamination since there is no later assembly. Following sterilization, the sterilizing chamber is evacuated to remove any traces of ethylene oxide gas from the syringe. It is then filled, asceptically through its open lower end with vaccine diluted to a concentration suitable for human administration. After being filled, the contents of the syringe 10 are frozen and lyophilized in known manner and the open end of the syringe then sealed by heated platens along the line indicated at 22 under anhydrous conditions.

The thus filled syringe, along with a plurality of other syringes similarly processed and filled, is placed into a gas, moisture and light impervious bag 30 as shown in FIG. 5. The protection from carbon dioxide gas is of particular importance when dry ice is used to maintain the low temperature of the entire assembly during shipment. The carbon dioxide, if it permeates the container portion of the syringe, may adversely affect the pH of the vaccine and its titer. The bag 30 and its contents are then sealed.

Following this sealing operation the bag 30 is placed in an environment maintained at a temperature of below about 8° C, typically from about −20° C to about 8° C, either by a mechanical freezer or by placing the bag 30 in a container of dry ice. As long as the bag 30 is maintained at these freezing temperatures, the lyophilized vaccine in the syringes does not deteriorate. Further, because the syringes do not depend upon plunger type actuation, any changes in dimensional relationships between the various syringe components is accommodated without impairment of the final use of the syringes.

The outer bag is to made of a material which is impervious to light, moisture and gas. One such example is the bag 30 shown in FIG. 6 which is basically made of metal foil, such as aluminum foil. This material protects the vaccine in the syringes from moisture, light and undesirable gases, which is released by sublimation of the dry ice which might otherwise penetrate the syringe material and reduce the effectiveness of the vaccine. It is obvious, therefore, that the present invention provides an individual delivery system which would cost only a fraction of the delivery system now in use.

In one embodiment of the invention, the bag 30 is of a triple layer material, as can be seen in FIGS. 5 and 6. Thus, the bag 30 has an outer layer 32 of a high density protective plastic material such as polyethylene terephthalate which is sold under the trademark "Mylar." This outer layer, which protects the bag 30 from abrasion and scuffing is preferably about 0.5 mil thick. The outer layer 32 is bonded to a main foil layer 34, preferably of aluminum, having a thickness of about 0.35 mil. The aluminum foil layer 34 serves to prevent entry of light, moisture or carbon dioxide gas into the bag. The foil layer 34 is bonded to an inner layer 36 of polyolefin material, such as low density polyethylene, about 3 mil thickness. The inner layer 36 is thermoplastic and serves to seal the edges of the bag 30 together under heat and pressure as shown in FIG. 6.

FIG. 7 shows the bag 30 sealed around a plurality of syringes containing the lyophilized vaccine.

FIG. 8 shows a container 37 for water for injection for use in conjunction with the vaccine delivery system of the present invention. The container 37 is formed of a backing sheet 38 having a blister pack 39 formed of vinyl plastic. The container is filled in conventional fashion with at least enough water for injection 40 to reconstitute the lyophilized vaccine in one syringe.

FIG. 9 shows another container 41 for water for injection. This container is formed of low density polyethylene or polypropylene filled in conventional fashion with at least enough water for injection 42 to reconstitute the lyophilized vaccine in one syringe.

It will be appreciated that the above described vaccine delivery system provides preloaded single dosage syringe units which are ready for injection with no preparatory manipulation required other than to puncture the syringe, remove the dust guard and draw water for injection into the syringe. The dosage concentration of the vaccine is thus fixed at the site of manufacturing and is not dependent upon vagaries at administration. During storage and shipment of the vaccine containing syringes of the present invention, moreover, there is no danger of leakage of vaccine.

Although specific embodiments of the invention are herein disclosed for purposes of explanation, various modifications thereof, after study of this specification, will be apparent to those skilled in the art to which the invention pertains.

What is claimed is:

1. A vaccine delivery system suitable for human administration comprising a hypodermic syringe having a single dosage container portion made of a plastic material which is resiliently flexible at room temperature and a needle portion comprising a hollow sharp needle extending from the plastic container portion to convey fluids from within the container out through the tip of the needle when the needle is inserted under the skin and the container is squeezed, a vaccine in an amount suitable for human administration sealed within the container, the vaccine being in the lyophilized state, whereby the vaccine is preserved for storage and shipment and the syringe is protected from leakage during storage and shipment, and a separate container of a single dose of water for injection to reconstitute the lyophilized vaccine in the hypodermic syringe.

2. A vaccine delivery system according to claim 1 wherein said vaccine is at a temperature of below about 8° C.

3. A vaccine delivery system according to claim 1 wherein said container portion is composed of low density polyethylene.

4. A vaccine delivery system according to claim 1 wherein the container for the water for injection is formed of low density polyethylene.

5. A vaccine delivery system according to claim 1 wherein the container for the water for injection is formed of a vinyl blister pack.

6. A vaccine delivery system according to claim 1 wherein the container for the water for injection is formed of polypropylene.

7. In combination, a plurality of single dosage hypodermic syringes each comprising a tubular container portion of plastic material which is resiliently flexible at room temperature and a needle portion comprising a hollow sharp needle extending out from the container portion, a single dosage of a lyophilized vaccine suitable for human administration contained in each tubular container portion and sealed therein, and a gas, moisture and light impervious bag enveloping the plurality of syringes and sealing the syringes therein.

8. A combination according to claim 7 wherein the gas, moisture and light impervious bag is of aluminum foil.

9. A combination according to claim 7 wherein the syringes include removable dust covers enveloping the outer end of their needle portion.

10. A method of preparing vaccine for delivery storage and administration comprising the steps of filling a plurality of single dosage, tubular, flexible, hypodermic syringes with an aqueous vaccine diluted to human administration concentrations, freezing the vaccine, lyophilizing the vaccine, sealing the syringes closed under anhydrous conditions, and enveloping and sealing a plurality of the filled and sealed syringes inside a gas, moisture and light impervious bag.

11. A method according to claim 10 further including the step of subjecting the syringe to an ethylene oxide atmosphere prior to filling.

12. A method according to claim 11 further including the step of subjecting the syringe to a vaccum to purge the syringe of ethylene oxide.

* * * * *